(12) United States Patent
Raynal et al.

(10) Patent No.: US 12,151,994 B2
(45) Date of Patent: Nov. 26, 2024

(54) METHOD FOR OLIGOMERISING OLEFINS IN AN OLIFOMERISATION REACTOR

(71) Applicant: IFP Energies nouvelles, Rueil-Malmaison (FR)

(72) Inventors: Ludovic Raynal, Rueil-Malmaison (FR); Philippe Pagnier, Rueil-Malmaison (FR); Yozika Glavan Moreno, Rueil-Malmaison (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 198 days.

(21) Appl. No.: 17/774,509

(22) PCT Filed: Oct. 2, 2020

(86) PCT No.: PCT/EP2020/077706
§ 371 (c)(1),
(2) Date: May 5, 2022

(87) PCT Pub. No.: WO2021/089255
PCT Pub. Date: May 14, 2021

(65) Prior Publication Data
US 2022/0388928 A1    Dec. 8, 2022

(30) Foreign Application Priority Data

Nov. 6, 2019    (FR) ...................................... 1912417

(51) Int. Cl.
*C07C 2/08*          (2006.01)
*F04D 31/00*        (2006.01)

(52) U.S. Cl.
CPC ................ *C07C 2/08* (2013.01); *F04D 31/00* (2013.01)

(58) Field of Classification Search
CPC ... C07C 2/08; C07C 2/32; F04D 31/00; Y02P 20/582
See application file for complete search history.

(56) References Cited

U.S. PATENT DOCUMENTS 4,948,394 A     8/1990  Rojey
2012/0199467 A1  8/2012  Gildenhuys et al.
(Continued)

FOREIGN PATENT DOCUMENTS

| EP | 2488473 A1 | 8/2012 |
| EP | 2703373 A1 | 3/2014 |
| FR | 2570162 A1 | 3/1986 |

OTHER PUBLICATIONS

English Translation of International Search Report for PCT/EP2020/077706 dated Jan. 18, 2021.
(Continued)

*Primary Examiner* — Ali Z Fadhel
(74) *Attorney, Agent, or Firm* — Millen, White, Zelano & Branigan; Csaba Henter

(57) ABSTRACT

The present invention relates to a process for the oligomerization of C2 to C4 olefin(s) in a gas/liquid or all-liquid oligomerization reactor (c) using a solvent, an oligomerization catalyst and olefin(s), in which compression and premixing are performed between a liquid phase comprising the solvent and a gaseous phase comprising said gaseous olefin (s) by a multiphase pump (b), with partial or total dissolution of the olefin(s) of the gaseous phase in the liquid phase and/or premixing between the two phases, before introduction of the premix obtained into said reactor.

20 Claims, 5 Drawing Sheets

(56) References Cited

U.S. PATENT DOCUMENTS

2014/0012059 A1    1/2014  Vinel et al.
2022/0089509 A1*  3/2022  Kim .......................... C07C 2/06

OTHER PUBLICATIONS

Battsengel, B. et al., "Utilization of a Two-phase Reactor with Pre-saturator for Multiphase Reactions," Chemical Engineering and Technology, May 1, 2004, vol. 27, No. 5, pp. 490-495.

Behr, A. et al. "Dreiphasige Butadien-Telomerisationen im Kontinuierlich betriebenen Schlaufenreaktor," Chemie Ingenieur Technik., Oct. 1, 2008, vol. 80, No. 10, pp. 1509-1517.

* cited by examiner

METHOD FOR OLIGOMERISING OLEFINS IN AN OLIFOMERISATION REACTOR

TECHNICAL FIELD

The invention relates to the field of oligomerization of olefins such as ethylene. This oligomerization is directed towards producing α-olefins, which are used as comonomers in processes for producing various grades of polyethylene. The invention is more particularly directed towards the oligomerization of ethylene to give linear α-olefins, such as 1-butene, 1-hexene or 1-octene, or a mixture of linear α-olefins.

The oligomerization reaction is usually performed in a homogeneous catalysis process, notably in the liquid phase. It is moreover highly exothermic, generally requiring external cooling via heat exchangers.

PRIOR ART

The invention relates to the field of oligomerization processes using gas/liquid reactors, in general with an implementation of bubble columns. Due to the exothermic nature of the oligomerization reactions, bubble columns also generally comprise a recirculation loop that consists in withdrawing a liquid fraction, cooling it by means of exchangers and reintroducing it into the reaction chamber/reactor. Said recirculation loop makes it possible to obtain good homogeneity of the concentrations and to control the temperature throughout the reaction volume, due to the good heat transfer capacity related to the recirculation loop. The installation also generally comprises, downstream of the oligomerization reactor, one or more separating columns, for isolating the desired reaction products, and optionally for recycling the solvent and/or the unreacted ethylene. Installations of this type are described, for example, in patents EP-2 703 373 and EP-3 338 884.

Oligomerization processes with this type of gas/liquid reactor still have room for improvement. Thus, the gaseous phase which is in the top part of the reactor, also known as the "gaseous headspace", comprises the gaseous compounds that are sparingly soluble in the liquid phase, compounds that are partially soluble in the liquid but inert, and also gaseous ethylene not dissolved in said liquid, which has not reacted and which has "risen" directly from the liquid phase in the bottom part of the reactor to the gaseous phase in the top part thereof. This direct passage of the gaseous ethylene from the liquid phase to the gaseous phase (or headspace) is a phenomenon known as piercing. This piercing is notably possible if the height of the bubble column or if the stirring therein are too low/insufficient for the ethylene bubbles to be totally absorbed in the liquid. Now, the gaseous headspace is regularly purged: When the amount of gaseous ethylene present in the headspace is substantial (with an associated increase in pressure), purging of the headspace leads to a significant loss of ethylene, which is detrimental towards the productivity of the oligomerization process. This purging may take place sequentially or continuously. In the latter case, it is then a matter of a purge equivalent in flow rate to a very small amount of the flow rate of ethylene entering, generally less than 5%, and preferably as low as possible.

Moreover, the conversion of ethylene is rarely total, and recycling of this gas may be envisaged in the fractionation step downstream of the reaction section. Finally, a certain number of oligomerization processes use a solvent which, itself also, is recycled from the fractionation section to the reaction section.

Moreover, to improve the performance of the oligomerization process, there is a tendency to separate the unreacted ethylene from the reaction mixture withdrawn from the reactor, for example with a separating column, and to reinject this ethylene into the oligomerization reactor inlet to recycle it in order to improve its degree of conversion. However, it is not always possible to reinject it directly, since, once separated, in certain configurations, it may be at a lower pressure than the reactor pressure, and it is then necessary to compress it before injection, with an appropriately dimensioned compressor. It turns out that the investment cost (dimensioning of the compressor) and the running cost of the compressor (its electrical consumption) to compress the recycled ethylene is not negligible and emburdens the viability of the process. (In other configurations, however, the reactor may be at a lower pressure, then permitting direct recycling of ethylene from the separating column to the reactor.)

Moreover, the oligomerization processes may use solvents, for instance, but in a non-limiting manner, cyclohexane, which is used in the reaction section in order to improve the process performance, notably to obtain a gain in selectivity for a given conversion. The solvent is separated from the various components (unreacted ethylene, targeted α-olefins and other products generated in the reaction section) in the fractionation section downstream of the reaction section, and then, once separated, returned into the latter section.

In the context of the present text, the term "reaction section" refers to the reactor(s) of gas/liquid type, with a single reactor or several reactors in series and/or in parallel, and also the associated equipment thereof, and notably, in the case of the oligomerization processes with which the invention is concerned: —the cooling loop comprising one or more heat exchangers and associated with (each of) the reactor(s) to control the reaction exothermicity, —the means for introducing the catalyst into the reactor(s), for example in the form of an introduction loop, which may or may not be separate from the cooling loop, —means external to the reactor for separating/neutralizing the catalyst.

In the context of the present invention, the term "fractionation section" denotes the separating device(s), notably by distillation, arranged downstream of the reaction section, with a single device or a plurality of devices arranged in series and/or in parallel, these devices possibly being identical or different in their dimensioning or their design/functioning.

In the context of the present invention, the terms "upstream" and "downstream" are understood as a function of the general direction of flow of the reaction fluid in the production unit.

The aim of the invention is then to improve the ethylene oligomerization process in a gas/liquid reactor or in an all-liquid reactor. The invention seeks notably to improve the productivity/viability of the process, notably so as to avoid the phenomenon of piercing and/or to limit the investment and/or running costs of the process.

SUMMARY OF THE INVENTION

One subject of the invention is a process for the oligomerization of C2 to C4 olefin(s), notably ethylene, propylene or butene (or a mixture of at least two of these olefins) in a gas/liquid or all-liquid oligomerization reactor starting with a solvent, an oligomerization catalyst and ethylene. This process is such that compression and premixing are performed between a liquid phase comprising the solvent and a gaseous phase comprising the gaseous olefin(s) by a multiphase pump (b), with partial or total dissolution of the olefin(s) of the gaseous phase in the liquid phase and/or premixing between the two phases, before introduction of the premix obtained into said reactor.

In other words, according to one embodiment, the process of the invention is a process for the oligomerization of olefin(s) containing between 2 and 4 carbon atoms to linear α-olefins, performed by placing in contact a solvent, an oligomerization catalyst and said olefins, comprising:
- a step of partial or total dissolution (saturation) with olefins of said solvent by using a multiphase pump (b),
- a step of placing the olefin-saturated solvent in contact with the oligomerization catalyst in a gas/liquid or all-liquid oligomerization reactor (c).

In the rest of the present text, when ethylene is specifically mentioned, for the sake of brevity, all C2 to C4 olefins are also intended, thus also propylene and butenes, more particularly 1-butene.

It should also be noted that these (C2 to C4) olefins are also understood to be either only one of these olefins (for example only ethylene) or a mixture of at least two of these olefins (for example an ethylene+propylene mixture).

It should also be noted that the oligomerization catalyst may include several components, and is also referred to without preference as a catalytic (oligomerization) system.

The invention thus proposes to make use of a multiphase pump for premixing the liquid phase and the gaseous phase which feed the reactor. A multiphase pump (also known as MPP) is a multi-stage axial rotodynamic compression machine. Unlike conventional machines (pump and compressor which are used, respectively, for fluids that are very predominantly liquid or fluids that are very predominantly gaseous, i.e. with more than 90% and often more than 95% of the predominant phase), its design makes it possible to work mixtures of liquid and gas over a very broad volume fraction range, ranging from 0% to 100%. The pump includes an arrangement of several compression series, each composed of compression stages that are all identical per series. Each stage is itself composed of a rotating element (impeller) and of a static element (rectifier). The dimensioning of the machine is based on a certain number of geometrical parameters governed by criteria known to those skilled in the art. More precisely, depending on the conditions at the inlet of the pump imposed by the process and the pressure rise that the multiphase pump must achieve, the following are adjusted: the number of series of stages, i.e. the number of identical groups of stages, the number of stages per series, the outside diameter, the diameter of the hub inlet, the angles of the leading and trailing edges of the rotor blades, the rotation speed, and also passage cross section ratios. These parameters are input data for the use of a digital code dedicated to the generation of a two-phase compression stage geometry. Once the geometry has been created, it is checked and validated by using criteria defined to ensure the correct functioning of the compression stage when mixtures of gas and liquid are used with a given gas volume fraction (GVF). It is recalled that the GVF is calculated in the following manner:

$$\text{GVF} = Q_{gaz} \text{ (m}^3\text{/h)} / Q_{\text{total}} \text{ (m}^3\text{/h)}$$

This type of pump is already well known, and various designs of MPP are described, for example, in patents FR-2 471 501, U.S. Pat. Nos. 4,365,932, 4,641,679, FR-2 665 224, U.S. Pat. No. 5,375,976 and FR-2 748 533.

Their use in the field of oil/natural gas production has already been proposed. It has notably already been described in patents EP-0 917 905 and FR-0 860 442, in the context of processing oil/natural gas effluent containing impurities such as acidic gases, carbon dioxide and/or hydrogen sulfide, to perform the two-phase compression of a soluble gas (acidic gases) in a liquid (aqueous phase, byproduct of the processing of the oil effluent), the object being to reinject the liquid mixture obtained into a production well or into an underground cavity.

However, it had not been envisaged hitherto to use such pumps in other fields, notably in the field of petrochemistry, for example in ethylene oligomerization processes. The invention thus makes it possible, in the latter case, to ensure the premixing of a gaseous reagent, namely ethylene, and of its solvent, at the reactor inlet.

This use proved to be very advantageous in several respects: the MPP makes it possible to compress the mixture up to the pressure level prevailing in the oligomerization reactor, and, at the same time, to dissolve the gaseous ethylene in the solvent. A phase which may be very predominantly or even preferably entirely liquid is thus injected into the reactor, via a single inlet (including one or more injection points): the ethylene thus dissolved reacts better, more completely than in the form of gas bubbles. By reducing or even eliminating the ethylene gas bubbles in the reactor, the risks of piercing are greatly reduced, or even eliminated. The yield is thereby improved. It should be noted, however, that, depending on the configuration and the dimensioning of the reactor, a single inlet may be envisaged via a single injection point into the reactor, fed with the stream at the outlet of the MPP, or several inlets may be envisaged via several injection points with the ad hoc fluid connections between the outlet of the MPP and these multiple injection points.

In addition, and as detailed later, the MPP may be used to mix with the solvent not only fresh ethylene but also optionally recycled ethylene, recovered by separation downstream of the oligomerization reactor. In the latter case, the MPP becomes charged, at least partly, from the pressurization of the recycled ethylene. In the case where the reactor is at relatively high pressure (in other cases, the reactor functions at low/lower pressure), and when it is therefore necessary to compress the recycled ethylene before reinjecting it into the reactor, the invention makes it possible to use a compressor for the pressurisation of the recycled ethylene before reinjection into the reactor, which does not require as much power as conventionally. It is thus possible to use a compressor of smaller size and of lower energy consumption, or even to dispense with the compressor completely, which is, in terms of investment and of running costs, very advantageous.

Preferably, the multiphase pump ensures total dissolution of the gaseous ethylene in the liquid phase, until an entirely liquid phase is obtained at the pump outlet. This is the most advantageous configuration, which eliminates the risks of piercing and optimizes the ethylene/catalyst contact in the same liquid phase.

Preferably, the multiphase pump (b) is fed with the liquid phase and the gaseous phase in relative proportions corresponding to a gas volume fraction GVF of at least 5%. This gas volume fraction GVF may rise up to 50%, 60% and even 80% if need be. The advantage of this type of pump is, precisely, that it enables a liquid phase to be mixed with a very high, predominant, proportion of gas. There is thus no need to adapt the ratio between the solvent and olefins (ethylene) relative to the conventional operating conditions; a high proportion of ethylene may be conserved, which is clearly advantageous (it is thus possible to conserve the same reactor dimensioning, the same entering flow rate of olefins relative to its solvent, while at the same time increasing the reaction yield).

The multiphase pump may ensure a rise in pressure of the mixture of the liquid phase and of the gaseous phase up to the pressure in the oligomerization reactor, notably up to a pressure of at least 20 bar absolute, and even up to 30, 40, 50 or 60 bar absolute or more. (The pressure in "bar absolute" is also written in abbreviated form as "bara"). Specifically, the choice of the pressure prevailing in the oligomerization reactor depends on a certain number of parameters (in particular the compounds under consideration, the catalytic performance of the catalyst (activity, conversion and selectivity), its concentration, the solvent content), but it is generally at least 20, 40 and even occasionally greater than 60 bara.

Advantageously, the liquid phase and the gaseous phase which are compressed and premixed by the multiphase pump (b) before introduction into the reactor comprise at least partly, respectively, recycled solvent and/or recycled ethylene (C2-C4 olefins), which is/are recycled by separation downstream of the reactor.

A first separation may be performed, notably by one or more first fractionation columns downstream of the reactor (c), of the reaction mixture obtained from the oligomerization performed in the reactor (c), said mixture comprising the C2-C4 olefin(s) (ethylene), solvent, an oligomerization catalyst, and oligomerization products, so as to obtain a head fraction containing the olefin(s) (ethylene) and at least one tail fraction. Any known separation means may be used to do this, such as a distillation column downstream of the reactor. The aim of this separation is to recover the unreacted C2-C4 olefin(s) (ethylene).

A second separation of at least a portion of the tail fraction obtained from the separation of the mixture may be performed, notably with one or more second fractionating column(s) downstream of the first column(s), into at least a head fraction enriched in oligomerization products and a tail fraction enriched in solvent. Any known separation means may be used to do this, such as another distillation column downstream of the preceding one. The aim of this separation is to recover the solvent, in order to reuse it.

It should be noted that, depending on the type of fractionating scheme chosen in the fractionating section, to be adapted as a function of the desired products, the separation of the solvent may be performed in the second separation or in an $n^{th}$ separation, performed downstream of the reaction section, at the top of the column or at the bottom of the column; the terms "first" and "second" separation are thus not to be understood literally and are merely indicated to mean that one takes place downstream of the other, but not necessarily consecutively.

At least a portion of the head fraction containing the C2-C4 olefin(s) (ethylene), known as the recycled olefin(s) (ethylene), obtained from the first separation, may be recycled, these recycled olefins then possibly forming part of the gaseous phase on which the compression and premixing by the multiphase pump are performed. This gaseous fraction is essentially composed of the C2-C4 olefin(s) (ethylene), but may also comprise traces of heavier products (desired α-olefin, or other alkenes and/or alkanes produced by the reaction) and/or traces of solvent and/or traces of other compounds present in the ethylene feedstock (traces of methane, of ethane, etc.).

At least a portion of the tail fraction enriched in solvent, known as recycled solvent, obtained from the second, or $n^{th}$, separation, may be recycled; this recycled solvent may then form part of the liquid phase on which the compression and premixing by the multiphase pump are performed.

It is then possible to perform a second separation of at least a portion of the tail fraction obtained from the separation of the mixture of at least one head fraction enriched in oligomerization products and one tail fraction enriched in solvent, or of at least one head fraction enriched in solvent and one tail fraction enriched in oligomerization products (the latter case being notably when it is desired to separate the solvent from heavy products).

Advantageously, at least a portion of the tail fraction enriched in solvent, known as recycled solvent, obtained from the second separation may be recycled to form part of the liquid phase entering the oligomerization reactor, notably after optional compression (in the case, notably, where the oligomerization reactor operates at high pressure). This liquid fraction is essentially composed of solvent, but may also comprise traces of α-olefin(s) (ethylene), of reaction products or coproducts, and/or of the catalyst soluble in liquid medium. It is also possible for the solvent to be recovered at the top of the column, in the case of a separation between solvent and heavy products.

The process according to the invention thus seeks to optimize the recycling of the olefins (ethylene) and of the solvent by proposing to combine them, at least partially.

Preferably, the gaseous phase containing the gaseous α-olefin(s), such as gaseous ethylene, which is compressed and premixed by the multiphase pump, comprises one or more fresh C2-C4 olefins (fresh ethylene) and/or one or more recycled C2-C4 olefin(s) (recycled ethylene) at the reactor outlet.

Preferably, the multiphase pump is fed with gaseous phase and with liquid phase via a device for regulating the flow rate, or for regulating the liquid level, notably such as a gas/liquid mixing vessel, which is positioned upstream of said multiphase pump and is itself fed, on the one hand, with fresh C2-C4 olefins (fresh ethylene) or with recycled C2-C4 olefin(s) (recycled ethylene) or with a mixture of fresh C2-C4 α-olefin(s) and of recycled C2-C4 α-olefin(s) (for example a mixture of fresh ethylene and of recycled ethylene), and, on the other hand, with solvent, notably with recycled solvent. This vessel (or other equivalent device) makes it possible, on the one hand, to ensure placing in contact of the two gas and liquid phases so as to ensure feeding of the pump that is as stable as possible, and, on the other hand, to offer a "buffer" storage volume for a certain amount of gas and of liquid, making it possible to feed the pump even in the case of temporary operating problems.

A portion of the C2-C4 olefin(s) (gaseous ethylene) feeding the oligomerization reactor, notably all or part of the recycled C2-C4 olefin(s) (recycled ethylene), and/or all or part of the fresh C2-C4 α-olefin(s) (fresh ethylene), may be introduced at the outlet of the multiphase pump or at the inlet of the oligomerization reactor.

According to one embodiment, the C2-C4 olefin(s) (ethylene) feeding the oligomerization reactor is, partly, recycled C2-C4 olefins (recycled ethylene) which is (are) optionally compressed before reintroduction into said reactor.

According to one embodiment, the C2-C4 olefin(s) which are recycled (recycled ethylene) by separation at the reactor outlet is (are) compressed before introduction into the reactor by a plurality of n compressors in series, and the multiphase pump comprises a plurality of m successive stages, where, at the outlet of each of the n−1 compressors, a first stream feeds the next compressor and a second stream feeds the inlet of a stage of the multiphase pump. This thereby gives compressors in cascade, with, at the outlet of each compressor, a portion of the stream which feeds a stage of the MPP (the stages are fed successively, from upstream to downstream). The advantage of such a configuration is that of replacing a single compressor for the recycled C2-C4 olefins (recycled ethylene) with a series of smaller compressors, so as to reduce the operating flow rate of each of these "small" compressors relative to that of the single compressor, to reduce also, for each of these compressors, the pressure difference to be achieved, and to maintain a constant gas volume flow rate at each stage of the MPP, part of the gas having been dissolved in the liquid phase due to the very good level of stirring at each stage of the pump.

The multiphase pump is, for example, a two-phase pump comprising up to 3 series of compression stages, each comprising up to 5 identical compression stages, and a power from at least 100 kW up to 3000 kW: Its dimensioning is to be adjusted as a function of the liquid and gaseous phases to be premixed, which are associated with the dimensioning of the oligomerization reactor.

A subject of the invention is also an installation for the oligomerization of C2 to C4 olefins, comprising a reactor for gas/liquid or all-liquid oligomerization using a solvent, an oligomerization catalyst and C2-C4 olefins (ethylene), such that said installation comprises a multiphase pump ensuring the compression and premixing between a liquid phase comprising the solvent and a gaseous phase comprising the gaseous C2-C4 olefin(s) (such as gaseous ethylene), with partial or total dissolution of the C2-C4 olefin(s) (ethylene) of the gaseous phase in the liquid phase and/or premixing between the two phases, for introduction of the premix obtained into said reactor.

A subject of the invention is also an installation for performing the process described above, which comprises: —at least one oligomerization reactor using C2 to C4 olefins, solvent and oligomerization catalyst, —at least two successive separation columns in series downstream of the oligomerization reactor, —at least one gas/liquid mixture vessel fed with recycled solvent obtained from the second separation column and with fresh ethylene and/or recycled ethylene obtained from the first separation column, said vessel feeding a multiphase pump, —said multiphase pump fed with fresh C2-C4 olefins (fresh ethylene) and/or recycled C2-C4 olefins and with fresh and/or recycled solvent at least partly via the gas/liquid mixture vessel and feeding the reactor.

Preferably, the gaseous phase containing the C2-C4 olefin(s) (such as gaseous ethylene) which is compressed and premixed by the multiphase pump before introduction into the oligomerization reactor is one or more fresh C2-C4 olefins (fresh ethylene) and/or recycled C2-C4 olefins (recycled ethylene) leaving the oligomerization reactor, notably either one or more fresh C2-C4 olefins (such as fresh ethylene) or a mixture of fresh and recycled C2-C4 olefin(s) (such as a mixture of fresh ethylene and recycled ethylene).

In the latter case, as mentioned above, since the MPP can ensure the pressure rise up to that of the reactor, it may be permitted to under-dimension or even to omit the compressor which was conventionally used for recompressing the C2-C4 olefin(s) such as recycled ethylene before reinjection. The MPP can thus replace this compressor, or at the very least enable it to compress to a lower pressure the C2-C4 olefin(s) such as recycled ethylene.

Preferably, the portion of liquid phase which is compressed and premixed by the multiphase pump before introduction into the oligomerization reactor is at least partly solvent recycled by separation at the oligomerization reactor outlet.

It is then possible to conserve a single inlet to reagent and solvent into the oligomerization reactor, whether it is "fresh" reagent/solvent or recycled reagent/solvent, which simplifies the running and design of the reactor.

Ethylene recycled by separation at the outlet of the oligomerization reactor, and preferably compressed beforehand, may also be either introduced directly into the multiphase pump (with or without prior compression) or added to the stream leaving the multiphase pump (in this case it will have been compressed beforehand), the whole feeding the oligomerization reactor.

The liquid phase in the oligomerization reactor preferably has a degree of saturation of the liquid phase with gaseous ethylene of at least 70%, and if possible of at least 90%. This is a very high degree, obtained by means of the good quality of mixing in the reactor, and/or obtained by means of the premixing with an MPP according to the invention, which induces a high degree of conversion of the C2-C4 olefin(s) (such as ethylene).

Preferably, the oligomerization in the reactor is performed at a pressure of between 0.1 and 10.0 MPa and at a temperature of between 30 and 200° C.

The invention will be described with the aid of non-limiting examples of the oligomerization process under consideration, illustrated by the figures listed below.

BRIEF DESCRIPTION OF THE DRAWINGS

FIGS. 1 to 8 are very schematic and notably represent the various components of the installations without necessarily being to scale or representing the relative spatial configuration of the components under consideration, and being confined to representing the most important components for the purposes of the invention, so as to facilitate the reading thereof. Thus, notably, none of the figures shows the cooling loop external to the oligomerization reactor which is necessary for controlling the exothermicity of the reaction in the reactor, or the catalyst injection system, or the fluid introduction means, which are known per se in oligomerization installations. It should be noted that the references keep the same meaning from one figure to another.

Figure 1:
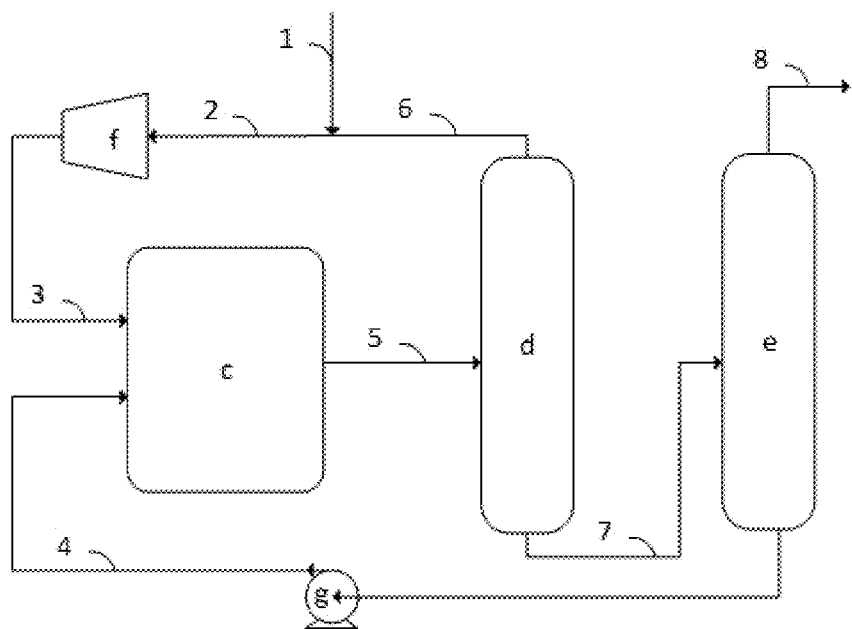
FIG. 1 is a diagram of an ethylene oligomerization installation according to the prior art.

Moreover, it should be noted that the fractionation scheme may be more complex and may include more than two columns; it may also incorporate additional separating means other than columns, directed notably towards separating the spent catalyst from the reaction products and coproducts, for instance flashes, thin-film evaporators or any other technology known to those skilled in the art.

Definitions, Abbreviations and Conventions in the Context of the Present Invention The multiphase pump may be denoted by its abbreviation MPP. In all the examples, it is a liquid/gas two-phase pump.

The terms "upstream" and "downstream" should be understood as a function of the general flow of the fluid under consideration in the installation, from the introduction of the reagents, such as ethylene in this case, up to the recovery of the product of interest, namely the α-olefin under consideration in the process.

The oligomerization corresponds to any reaction for the addition of a first olefin to a second olefin identical to or different from the first olefin. The olefin thus obtained has the empirical formula $C_nH_{2n}$, where n is equal to or greater than 4. The examples concern the main reaction of ethylene with itself to produce 1-butene and/or 1-hexene and/or higher oligomers.

An α-olefin (in this case the product obtained after oligomerization) is an olefin in which the double bond is located in the terminal position of the alkyl chain.

In the examples, the oligomerization catalyst is a mixture (also known as a catalytic system) of at least one metal precursor and of at least one activating agent, optionally in the presence of at least one additive and optionally of a solvent.

The liquid phase corresponds to the mixture of all of the compounds that are in a liquid physical state under the temperature and pressure conditions of the reaction section, including the entering fluid streams including those coming from the MPP and from the gas/liquid mixture vessel (including the streams recycled from downstream of the reaction section) and the streams exiting towards the fractionating section.

The gaseous phase may correspond to the mixture of all of the compounds which are in a gaseous physical state under the temperature and pressure conditions of the reaction chamber (oligomerization reactor), which is in the form of bubbles present in the liquid phase, notably in the abovementioned entering streams, and also in one-phase form in the streams entering/exiting the reactor and optionally in the top part of the reactor (known as the "gaseous headspace" of the reactor).

As already seen, the oligomerization reaction section comprises the oligomerization reactor and its equipment, including the cooling loop, the means for introducing/removing the various fluids and the catalyst, in its simplest version. The invention also includes a reaction section composed of several oligomerization reactors, in series and/or in parallel. For the sake of brevity, the term "reactor" may rather be used when referring to the reaction section.

A "fresh" component (ethylene, solvent) is a component not recycled from a downstream step of the oligomerization process to a step further upstream or during the same step.

In contrast, a "recycled" component is a component produced or separated out, which is present in a downstream step of the process and which is recycled from a given step of the process to a step further upstream in the process or during the same step (withdrawal of a reactor to refeed the same reactor, for example, notably with cooling of the stream). Recycled ethylene or solvent are to be considered as comprising, respectively, essentially ethylene and solvent, but being liable to comprise traces of other components.

For the sake of brevity, a detailed description will not be given hereinbelow of the entire oligomerization installation and of the operating conditions for its implementation which are not strictly linked to the invention: for further details regarding oligomerization as a whole, reference may be made notably to the abovementioned patents EP-2 703 373 and EP-3 338 884.

However, examples of reagent, solvent and catalyst and also the main modes of performing the oligomerization are given below: The oligomerization process according to the invention allows linear α-olefins to be obtained by placing in contact ethylene and a catalytic system, optionally in the presence of a solvent.

Any catalytic system known to a person skilled in the art and capable of being employed in the dimerization, trimerization or tetramerization processes and more generally in the oligomerization processes according to the invention falls within the field of the invention. Said catalytic systems and also the implementations thereof are notably described in the applications FR 2 984 311, FR 2 552 079, FR 3 019 064, FR 3 023 183, FR 3 042 989 or in the application FR 3 045 414.

Preferably, the catalytic systems comprise, preferably consist of:
a metal precursor, preferably based on nickel, on titanium or on chromium,
an activating agent,
optionally an additive, and
optionally a solvent.

The Metal Precursor

The metal precursor used in the catalytic system is chosen from compounds based on nickel, on titanium or on chromium.

In one embodiment, the metal precursor is based on nickel and preferably comprises nickel of (+II) oxidation state. Preferably, the nickel precursor is chosen from nickel(II) carboxylates, for instance nickel 2-ethylhexanoate, nickel (II) phenates, nickel(II) naphthenates, nickel(II) acetate, nickel(II) trifluoroacetate, nickel(II) triflate, nickel(II) acetylacetonate, nickel(II) hexafluoroacetylacetonate, π-allylnickel(II) chloride, π-allylnickel(II) bromide, methallylnickel(II) chloride dimer, η3-allylnickel(II) hexafluorophosphate, η3-methallylnickel(II) hexafluorophosphate and nickel(II) 1,5-cyclooctadienyl, in their hydrated or non-hydrated form, taken alone or as a mixture.

In a second embodiment, the metal precursor is based on titanium and preferably comprises a titanium aryloxy or alkoxy compound.

The titanium alkoxy compound advantageously corresponds to the general formula [Ti(OR)$_4$] in which R is a linear or branched alkyl radical. Among the preferred alkoxy radicals, non-limiting examples that may be mentioned include tetraethoxy, tetraisopropoxy, tetra(n-butoxy) and tetra(2-ethylhexyloxy).

The titanium aryloxy compound advantageously corresponds to the general formula [Ti(OR')$_4$] in which R' is an aryl radical substituted or unsubstituted with alkyl or aryl groups. The radical R' may comprise heteroatom-based substituents. The preferred aryloxy radicals are chosen from phenoxy, 2-methylphenoxy, 2,6-dimethylphenoxy, 2,4,6-trimethylphenoxy, 4-methylphenoxy, 2-phenylphenoxy, 2,6-diphenylphenoxy, 2,4,6-triphenylphenoxy, 4-phenylphenoxy, 2-(tert-butyl)-6-phenylphenoxy, 2,4-di(tert-butyl)-6-phenylphenoxy, 2,6-diisopropylphenoxy, 2,6-di(tert-butyl)phenoxy, 4-methyl-2,6-di(tert-butyl)phenoxy, 2,6-dichloro-4-(tert-butyl)phenoxy and 2,6-dibromo-4-(tert-butyl)phenoxy, the biphenoxy radical, binaphthoxy or 1,8-naphthalenedioxy.

According to a third embodiment, the metal precursor is based on chromium and preferably comprises a chromium (II) salt, a chromium(III) salt or a salt of different oxidation state which may comprise one or more identical or different anions, for instance halides, carboxylates, acetylacetonates or alkoxy or aryloxy anions. Preferably, the chromium-based precursor is chosen from $CrCl_3$, $CrCl_3(tetrahydrofuran)_3$, $Cr(acetylacetonate)_3$, $Cr(naphthenate)_3$, $Cr(2\text{-ethylhexanoate})_3$ and $Cr(acetate)_3$.

The concentration of nickel, of titanium or of chromium is between 0.01 and 300.0 ppm by weight of atomic metal, relative to the reaction mass, preferably between 0.02 and 100.0 ppm, preferably between 0.03 and 50.0 ppm, more preferably between 0.5 and 20.0 ppm and even more preferably between 2.0 and 50.0 ppm by weight of atomic metal, relative to the reaction mass.

The Activating Agent

Whatever the metal precursor, the catalytic system also comprises one or more activating agents chosen from aluminium-based compounds, such as methylaluminium dichloride ($MeAlCl_2$), dichloroethylaluminium ($EtAlCl_2$), ethylaluminium sesquichloride ($Et_3Al_2Cl_3$), chlorodiethylaluminium ($Et_2AlCl$), chlorodiisobutylaluminium ($i\text{-}Bu_2AlCl$), triethylaluminium ($AlEt_3$), tripropylaluminium ($Al(n\text{-}Pr)_3$), triisobutylaluminium ($Al(i\text{-}Bu)_3$), diethylethoxyaluminium ($Et_2AlOEt$), methylaluminoxane (MAO), ethylaluminoxane (EAO) and modified methylaluminoxanes (MMAO).

The Additive

Optionally, the catalytic system comprises one or more additives.

When the catalytic system is based on nickel, the additive is chosen from: compounds of nitrogenous type, such as trimethylamine, triethylamine, pyrrole, 2,5-dimethylpyrrole, pyridine, 2-methylpyridine, 3-methylpyridine, 4-methylpyridine, 2-methoxypyridine, 3-methoxypyridine, 4-methoxypyridine, 2-fluoropyridine, 3-fluoropyridine, 3-trifluoromethylpyridine, 2-phenylpyridine, 3-phenylpyridine, 2-benzylpyridine, 3,5-dimethylpyridine, 2,6-di(tert-butyl)pyridine and 2,6-diphenylpyridine, quinoline, 1,10-phenanthroline, N-methylpyrrole, N-butylpyrrole, N-methylimidazole, N-butylimidazole, 2,2'-bipyridine, N,N'-dimethylethane-1,2-diimine, N,N'-di(t-butyl)ethane-1,2-diimine, N,N'-di(t-butyl)butane-2,3-diimine, N,N'-diphenylethane-1,2-diimine, N,N'-bis(2,6-dimethylphenyl)ethane-1,2-diimine, N,N'-bis(2,6-diisopropylphenyl)ethane-1,2-diimine, N,N'-diphenylbutane-2,3-diimine, N,N'-bis(2,6-dimethylphenyl)butane-2,3-diimine or N,N'-bis(2,6-diisopropylphenyl)butane-2,3-diimine, or the compounds of phosphine type are independently chosen from tributylphosphine, triisopropylphosphine, tricyclopentylphosphine, tricyclohexylphosphine, triphenylphosphine, tris(o-tolyl)phosphine, bis(diphenylphosphino)ethane, trioctylphosphine oxide, triphenylphosphine oxide or triphenyl phosphite, or the compounds corresponding to the general formula (I) or a tautomer of said compound:

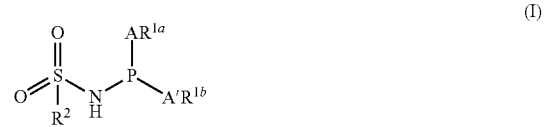

in which:
A and A', which may be identical or different, are independently an oxygen or a single bond between the phosphorus atom and a carbon atom,
the groups $R^{1a}$ and $R^{1b}$ are independently chosen from methyl, trifluoromethyl, ethyl, n-propyl, isopropyl, n-butyl, isobutyl, t-butyl, pentyl, cyclohexyl and adamantyl groups, which may or may not be substituted and may or may not contain heteroelements; phenyl, o-tolyl, m-tolyl, p-tolyl, mesityl, 3,5-dimethylphenyl, 4-(n-butyl)phenyl, 2-methylphenyl, 4-methoxyphenyl, 2-methoxyphenyl, 3-methoxyphenyl, 4-methoxyphenyl, 2-isopropoxyphenyl, 4-methoxy-3,5-dim ethylphenyl, 3,5-bis(tert-butyl)-4-methoxyphenyl, 4-chlorophenyl, 3,5-bis(trifluoromethyl)phenyl, benzyl, naphthyl, bisnaphthyl, pyridyl, bisphenyl, furyl and thiophenyl groups,
the group $R^2$ is independently chosen from methyl, trifluoromethyl, ethyl, n-propyl, isopropyl, n-butyl, isobutyl, t-butyl, pentyl, cyclohexyl and adamantyl groups, which may or may not be substituted and may or may not contain heteroelements; phenyl, o-tolyl, m-tolyl, p-tolyl, mesityl, 3,5-dimethylphenyl, 4-(n-butyl)phenyl, 4-methoxyphenyl, 2-methoxyphenyl, 3-methoxyphenyl, 4-methoxyphenyl, 2-isopropoxyphenyl, 4-methoxy-3,5-dimethylphenyl, 3,5-di(tert-butyl)-4-methoxyphenyl, 4-chlorophenyl, 3,5-bis(trifluoromethyl)phenyl, benzyl, naphthyl, bisnaphthyl, pyridyl, bisphenyl, furyl and thiophenyl groups.

When the catalytic system is based on titanium, the additive is chosen from diethyl ether, diisopropyl ether, dibutyl ether, diphenyl ether, 2-methoxy-2-methylpropane, 2-methoxy-2-methylbutane, 2,2-dimethoxypropane, 2,2-bis(2-ethylhexyloxy)propane, 2,5-dihydrofuran, tetrahydrofuran, 2-methoxytetrahydrofuran, 2-methyltetrahydrofuran, 3-methyltetrahydrofuran, 2,3-dihydropyran, tetrahydropyran, 1,3-dioxolane, 1,3-dioxane, 1,4-dioxane, dimethoxyethane, bis(2-methoxyethyl) ether, benzofuran, glyme and diglyme, taken alone or as a mixture.

When the catalytic system is based on chromium, the additive is chosen from:
compounds of nitrogenous type, such as trimethylamine, triethylamine, pyrrole, 2,5-dimethylpyrrole, pyridine, 2-methylpyridine, 3-methylpyridine, 4-methylpyridine, 2-methoxypyridine, 3-methoxypyridine, 4-methoxypyridine, 2-fluoropyridine, 3-fluoropyridine, 3-trifluoromethylpyridine, 2-phenylpyridine, 3-phenylpyridine, 2-benzylpyridine, 3,5-dimethylpyridine, 2,6-di(tert-butyl)pyridine and 2,6-diphenylpyridine, quinoline, 1,10-phenanthroline, N-methylpyrrole, N-butylpyrrole, N-methylimidazole, N-butylimidazole, 2,2'-bipyridine, N,N'-dimethylethane-1,2-diimine, N,N'-di(t-butyl)ethane-1,2-diimine, N,N'-di(t-butyl)butane-2,3-diimine, N,N'-diphenylethane-1,2-diimine, N,N'-bis(2,6-dimethylphenyl)ethane-1,2-diimine, N,N'-bis(2,6-diisopropylphenyl)ethane-1,2-diimine, N,N'-diphenylbutane-2,3-diimine, N,N'-bis(2,6-dimethylphenyl)butane-2,3-diimine or N,N'-bis(2,6-diisopropylphenyl)butane-2,3-diimine, or from aryloxy compounds of general formula [M(R³O)$_{2-n}$X$_n$]$_y$, in which:

M is chosen from magnesium, calcium, strontium and barium, preferably magnesium, R³ is an aryl radical containing from 6 to 30 carbon atoms and X is a halogen or an alkyl radical containing from 1 to 20 carbon atoms, n is an integer which can take the values of 0 or 1, and y is an integer between 1 and 10; preferably, y is equal to 1, 2, 3 or 4.

Preferably, the aryloxy radical R³O is chosen from 4-phenylphenoxy, 2-phenylphenoxy, 2,6-diphenylphenoxy, 2,4,6-triphenylphenoxy, 2,3,5,6-tetraphenylphenoxy, 2-(tert-butyl)-6-phenylphenoxy, 2,4-di(tert-butyl)-6-phenylphenoxy, 2,6-diisopropylphenoxy, 2,6-dimethylphenoxy, 2,6-di(tert-butyl)phenoxy, 4-methyl-2,6-di(tert-butyl)phenoxy, 2,6-dichloro-4-(tert-butyl)phenoxy and 2,6-dibromo-4-(tert-butyl)phenoxy. The two aryloxy radicals may be borne by the same molecule, for instance the biphenoxy radical, binaphthoxy or 1,8-naphthalenedioxy. Preferably, the aryloxy radical R³O is 2,6-diphenylphenoxy, 2-(tert-butyl)-6-phenylphenoxy or 2,4-di(tert-butyl)-6-phenylphenoxy.

The Solvent

In another embodiment according to the invention, the catalytic system itself optionally comprises one or more solvents. This or these solvents may help to introduce the catalyst into the reaction section, and are added to the actual solvent circulating in the MPP pump.

The solvent(s) are advantageously chosen from ethers, alcohols, halogenated (fluorinated, chlorinated, brominated or iodinated) solvents and aliphatic and cycloaliphatic hydrocarbons, comprising between 1 and 20 carbon atoms, preferably between 2 and 10 carbon atoms, preferably between 4 and 8, aromatic hydrocarbons comprising from 4 to 20 carbon atoms and preferably between 5 and 15 carbon atoms.

Preferably, the solvent is chosen from pentane, hexane, cyclohexane, methylcyclohexane, heptane, butane or isobutane, 1,5-cyclooctadiene, cyclopentadiene, benzene, toluene, ortho-xylene, mesitylene, ethylbenzene, diethyl ether, tetrahydrofuran, 1,4-dixoane, dichloromethane, chlorobenzene, methanol, ethanol, pure or as a mixture, and ionic liquids. The solvent is chosen from the group formed by aliphatic and cycloaliphatic hydrocarbons, such as hexane, cyclohexane, heptane, butane or isobutane.

Preferably, the solvent used is cyclohexane.

In one embodiment, a solvent or a mixture of solvents may be used during the oligomerization reaction. Said solvent is advantageously chosen independently from the group formed by aliphatic and cycloaliphatic hydrocarbons, such as hexane, cyclohexane, heptane, butane or isobutane.

Preferably, the linear α-olefins obtained comprise from 4 to 20 carbon atoms, preferably from 4 to 18 carbon atoms, preferably from 4 to 10 carbon atoms and preferably from 4 to 8 carbon atoms. Preferably, the olefins are linear α-olefins chosen from 1-butene, 1-hexene and 1-octene.

Advantageously, the oligomerization process is performed at a pressure of between 0.1 and 10.0 MPa, preferably between 0.2 and 9.0 MPa and preferably between 0.3 and 8.0 MPa, at a temperature of between 30 and 200° C., preferably between 35 and 150° C. and preferably between 45 and 140° C.

Preferably, the concentration of catalyst in the catalytic system is between 0.01 and 300.0 ppm by mass of atomic metal relative to the reaction mass, preferably between 0.02 and 100.0 ppm, preferably between 0.1 and 50.0 ppm, preferably between 0.03 and 50.0 ppm, even more preferably between 2.0 and 50.0 ppm, more preferably between 0.5 and 20.0 ppm, or between 0.4 and 30.0 ppm, or between 0.6 and 20.0 ppm, for example between 0.8 and 10.0 ppm or between 1.0 and 6.0 ppm by mass of atomic metal relative to the reaction mass.

According to one embodiment, the oligomerization process is performed batchwise. The catalytic system, constituted as described above, is introduced into the solvent inside a reactor equipped with the usual stirring, heating and cooling devices, then pressurization with ethylene is performed to the desired pressure, and the temperature is adjusted to the desired value. The oligomerization device is maintained at a constant pressure by introduction of gaseous ethylene until the total volume of liquid produced fills the desired fraction of the reaction volume. The catalyst is then neutralized by any usual means known to a person skilled in the art and the reaction products and the solvent are then withdrawn and separated.

According to another embodiment, the oligomerization process is performed continuously. The catalytic system, constituted as described above, is injected into a reactor stirred by conventional mechanical means known to a person skilled in the art or by external recirculation, and maintained at the desired temperature. The ethylene is also injected into the reactor via its own injection means. The components of the catalytic system can also be injected separately into the reaction medium and/or the solvent. The gaseous ethylene is generally introduced via a pressure-controlled intake valve, which keeps said pressure constant in the reactor or via an intake valve controlled by a flow-rate control. The reaction mixture is withdrawn by means of a liquid-level-control valve, so as to keep said level constant. The catalyst is neutralized continuously by any usual means known to a person skilled in the art and the products resulting from the reaction, and also the solvent, are then separated, for example by distillation. The ethylene which has not been converted may be recycled into the reactor. The catalyst residues included in a heavy fraction may be incinerated.

DESCRIPTION OF THE EMBODIMENTS

The examples and figures which follow concern, in a non-limiting manner, the oligomerization of ethylene.

As mentioned above, the invention applies mutatis mutandis to the oligomerization of other olefins such as propylene or butene, or a mixture of at least two thereof: the invention applies to C2 to C4 olefins, chosen from ethylene, propylene, 1-butene and 2-butene, isobutene, and preferably to ethylene.

FIG. 1 is a diagram of an installation implementing a conventional ethylene oligomerization process, which does not apply the invention: The main devices of the installation on which the invention will have an impact are shown in a simplified manner, namely a liquid/gas oligomerization reactor, a first separation (distillation) column d and a second separation (distillation) column e in series, a pump g and a compressor f. It does not show, and nor do the following FIGS. 2 to 8, the catalyst neutralization and separation section, which is well known per se.

The reactor c, which may be a series of reactors, and the two columns d and e define chambers which are substantially oriented along a vertical axis.

According to this diagram, and for purely illustrative purposes, the oligomerization reaction takes place in the reactor cat high pressure, in the region of 64 bar absolute.

The circulating streams are the following:

stream 1 is a stream of fresh ethylene stream 6 is a stream corresponding to the head fraction exiting the first column d, consisting essentially of ethylene (and of traces of compounds initially present in the fresh ethylene, and/or of solvent and of reaction products and coproducts), which will be recycled stream 2 is the mixture of stream 1 of fresh ethylene and of stream 6 of recycled ethylene stream 3 is stream 2 once it has been compressed to the desired pressure by the compressor f, and which enters the reactor c as a gaseous phase stream 5 is the stream withdrawn from the reactor c, which is a mixture of solvent, of catalyst, of unreacted ethylene and of reaction products stream 7 is the tail fraction obtained from the separation performed in the first column d; it includes the solvent, the catalyst and the reaction products the head stream 8 is the stream of reaction products separated in the second column e, in the case where these products are all lighter than the solvent the tail stream 4 is the stream of the solvent (and which may also contain traces of other compounds, notably of reaction products), which is separated in the second column e, which passes through a pump g and is then injected into an inlet of the reactor c as liquid phase.

The functioning of such an installation is as follows: The oligomerization reactor c is fed, on the one hand, with a gaseous phase 3 composed essentially of recycled ethylene 6 and of fresh ethylene 1, this phase having been compressed by the compressor f before injection at the operating pressure of the reactor c, namely in this case 64 bar absolute. The fresh ethylene of stream 1 before compression with the compressor f is at a pressure of 28 bar absolute, and the ethylene 6 is at a pressure of 8.5 bar absolute.

The reactor c is fed, on the other hand, with liquid phase, independently of the gaseous phase, this liquid phase consisting of stream 4 of solvent recycled through the pump g, the delivery pressure of which is 64 bar absolute. The operating temperature in the reactor is here, for example, equal to 135° C. The two columns d and e are schematics of a fractionation scheme which may be more complex, as mentioned above. Notably, this scheme does not show the device for separating the spent catalyst from the reaction products and the solvent. The two columns d and e shown make it possible, on the one hand, to isolate the reaction products 8 and, on the other hand, to recycle the unconverted ethylene (stream 6) and the solvent (stream 4).

This process functions, but nevertheless has drawbacks: the compressor f for compressing the ethylene 2 must be substantially dimensioned to allow the desired pressure rise of substantial flow rates of several tonnes per hour, or even several tens of tonnes per hour, and its energy consumption is significant.

The following are established in the liquid/gas reactor c:

a lower zone, which comprises a liquid phase, gaseous ethylene, and the reaction products such as the desired linear α-olefin (for example 1-butene, 1-hexene or 1-octene), the catalyst and the solvent (in this case, by way of example, cyclohexane)

and an upper zone, located at the top of the reactor c, i.e. directly above the lower zone and consisting of the gaseous headspace.

The principle of the reaction is that the gaseous ethylene must be absorbed in the liquid phase and placed in contact with the catalyst, and must be converted into reaction products before reaching the gaseous headspace. The reality is that there is a risk that the ethylene bubbles, those which are not dissolved in the solvent, rise directly into the gaseous headspace without conversion: this phenomenon is known as piercing.

The invention starts with the objective of reducing or even eliminating the need for the ethylene compressor f so as to reduce the investment and running cost of the process, and to minimize the piercing. To do this, different variants are envisaged, as illustrated in FIGS. 2 to 8.

Figure 2:
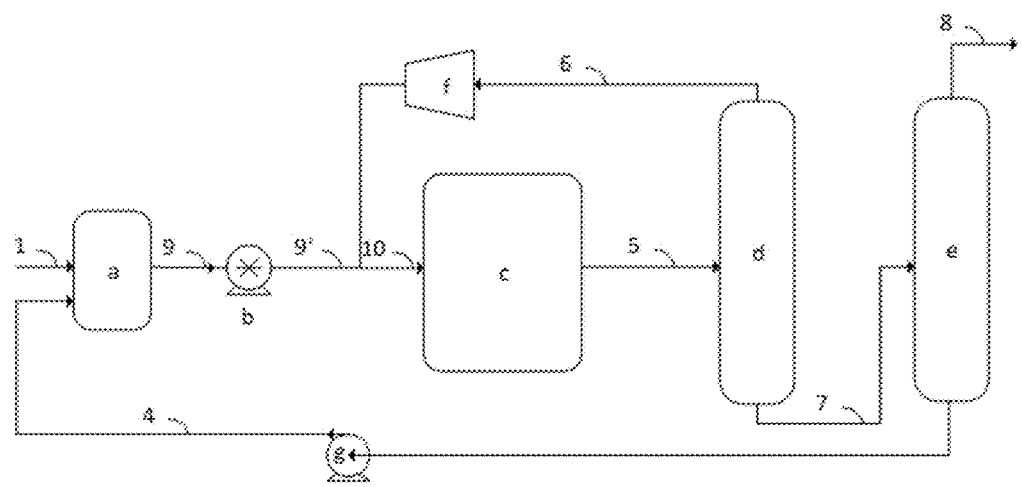
FIG. 2 is a diagram of an ethylene oligomerization installation according to a first variant of the invention.

FIG. 2 is a diagram of an installation implementing an ethylene oligomerization process according to a first variant of the invention. Attention will be focused above all on describing the differences from FIG. 1 of the prior art. According to this variant, it is sought to reduce the operating flow rate of the compressor f so as to reduce its cost. The installation has been modified so as to add a gas/liquid mixture vessel a and a multiphase pump b. Examples of suitable MPP pumps are described in the abovementioned patents FR-2 471 501, U.S. Pat. Nos. 4,365,932, 4,641,679, FR-2 665 224, U.S. Pat. No. 5,375,976 and FR-2 748 533.

The functioning of the installation has been modified in the following manner: the recycled solvent 4 is placed in contact with fresh ethylene 1 in the gas/liquid mixture vessel a. The recycled solvent 4 feeds the gas/liquid mixture vessel through the pump g, the delivery pressure of which is here 28 bar absolute. The two-phase stream 9 exiting the gas/liquid mixture vessel a is sent to the multiphase pump b to raise its pressure to 64 bar absolute, the stream thus compressed 9' exiting the multiphase pump b is mixed with the recycled ethylene 6 and compressed by the compressor f from a pressure of 8.5 bar absolute to a pressure of 64 bar absolute. The mixture 10 of stream 9' and of stream 6 is sent into the reactor c, which operates at 64 bar absolute via an inlet, either in the form of a single injection point, or in the form of multiple injection points intended to facilitate the distribution of the entering stream 10 throughout the volume of the reactor c. The mass flow rate of the liquid exiting the multiphase pump b is greater than the mass flow rate of liquid entering the pump b, on account of the dissolution of ethylene (total or partial) in the liquid. The most advantageous situation is that the stream 10 feeding the reactor c is totally liquid, which eliminates the risk of piercing of the bubbles in the reactor. Depending notably on the relative amount of the liquid solvent and of the gaseous ethylene entering the pump, there may be at the outlet either an entirely liquid stream, when all the ethylene has been able to be absorbed in the liquid, or a partially liquid and partially gaseous stream, with, in the liquid part, a variable amount of absorbed ethylene, and notably an amount which may correspond to saturation of the liquid with ethylene.

Pre-dimensioning of the multiphase pump MPP was performed using the pump inlet data, namely, by way of example, a pressure of 28 bar absolute, which corresponds here to the pressure at which the fresh ethylene is available, a temperature of 53.5° C., a total volume flow rate of 150 m$^3$/h for a gas volume fraction (GVF) of 58%. This pre-dimensioning of the MPP pump is chosen so as to be able to work this two-phase mixture and to reach a pressure of about 64 bar absolute at its outlet. The main geometrical parameters of the machine, in particular the casing diameter, the hub diameter and the rotation speed and the angles of the leading edges and trailing edge of the rotor blades, are estimated by successive calculation, stage by stage, by means of coupling three digital tools. The first tool dedicated to the thermodynamic stimulation makes it possible to determine for each operating condition the gas and liquid fractions and the coefficient of dissolution of the gas in the liquid, the second tool makes it possible to generate a two-phase compression stage geometry capable of compressing a mixture of liquid and gas under the conditions imposed by the process, and the third digital tool has the purpose of predicting the theoretical performance of the compression stage and of providing the thermodynamic conditions of the mixture for the next stage. Once the pump has been defined in its globality, the associated compression rate and the cost of the equipment are estimated, in terms of investment and power consumption.

Figure 3:
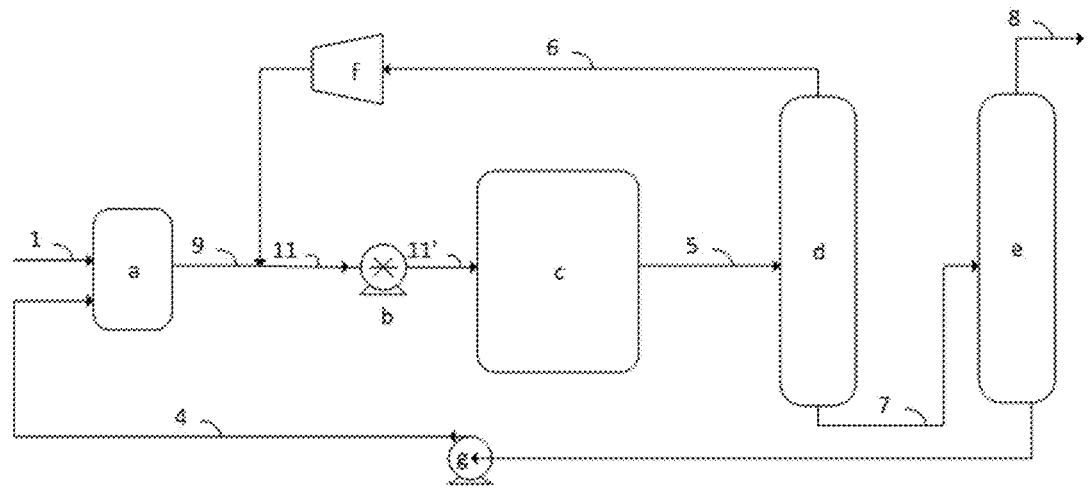
FIG. 3 is a diagram of an ethylene oligomerization installation according to a second variant of the invention.

FIG. 3 is a diagram of an installation implementing an ethylene oligomerization process according to a second variant of the invention. Attention will be focused above all on describing the differences with FIG. 2: the notable difference from the preceding variant is that, here, the recycled ethylene stream 6 is also processed by the MPP pump b (and, further, only the fresh ethylene 1, as regards the gaseous phase).

It is, in this case also, a matter of reducing the operating flow rate and the delivery pressure of the compressor f so as to reduce its cost. To do this, the solvent 4 is placed in contact with fresh ethylene 1 in the gas/liquid mixture vessel a as in FIG. 2. The solvent 4 is fed to the gas/liquid mixture vessel via the pump g, the delivery pressure of which is 28 bar absolute. The two-phase output 9 from the gas/liquid mixture vessel, at 28 bar absolute, is mixed as a stream 11 with the recycled ethylene stream 6, which has been compressed beforehand by the compressor f from 8.5 bar absolute to 28 bar absolute. The mixture 11 is sent to the multiphase pump b to raise its pressure to 64 bar absolute. The delivery 11' from the multiphase pump is sent to the reactor c, which operates at 64 bar absolute. The same pre-dimensioning procedure for the MPP pump as that used in the case of FIG. 2 is followed, considering, by way of example, a total volume flow rate of 353 m$^3$/h for a gas volume fraction (GVF) of 81%.

Figure 4:
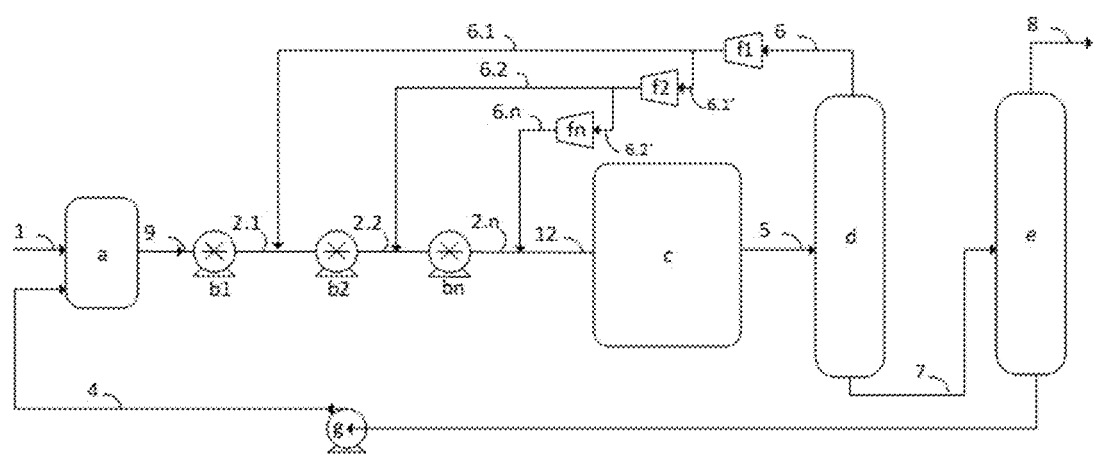
FIG. 4 is a diagram of an ethylene oligomerization installation according to a third variant of the invention.

FIG. 4 is a diagram of an installation implementing an ethylene oligomerization process according to a third variant of the invention. Attention will be focused above all on describing the differences with FIG. 3: the notable difference from the preceding variant is that, here, use will be made to compress the recycled ethylene 6 of not one single compressor but a series of small compressors, which cooperate with the stages of the pump b. These small compressors f1, f2, . . . fn make it possible to reduce the operating flow rate and the pressure difference of each of the compressors and to maintain a virtually constant gas flow rate in each stage of the multiphase pump b: The delivery pressure of each compressor f1, f2, . . . fn corresponds to the delivery pressure of each stage b1, b2, . . . bn of the multiphase pump b. The solvent 4 is placed in contact with fresh ethylene 1 in the gas/liquid mixture vessel a. The recycled solvent 4 feeds the gas/liquid mixture vessel a via the pump g, the delivery pressure of which is 28 bar absolute. The output from each stage of the multiphase pump 2.1, 2.2, . . . 2.n, is mixed with a portion of the recycled ethylene stream 6.1, 6.2, . . . 6.n exiting the various compressors (another portion of the stream 6.1', 6.2', . . . 6.n' exiting each of the compressors feeding the next compressor). In the example retained herein, the pressure difference in each stage of the multiphase pump b is in the region of 2 bar absolute. As a result, the first compressor f1 compresses the recycled ethylene from 8.5 bar absolute to 30 bar absolute, f2 compresses a portion of the recycled ethylene exiting f1 from 30 bar absolute to 32 bar absolute, etc. The delivery of the last stage of the multiphase pump b is sent to the reactor c, which operates at 64 bar absolute. Stream 12 entering the reactor c is the mixture of the stream exiting from the last stage of the MPP pump b and from the last compressor fn.

The pre-dimensioning of the MPP pump b necessary for the variant according to FIG. 4 leads to a pump of 23 compression stages divided into two series, for a power of the order of 865 kW.

Figure 5:
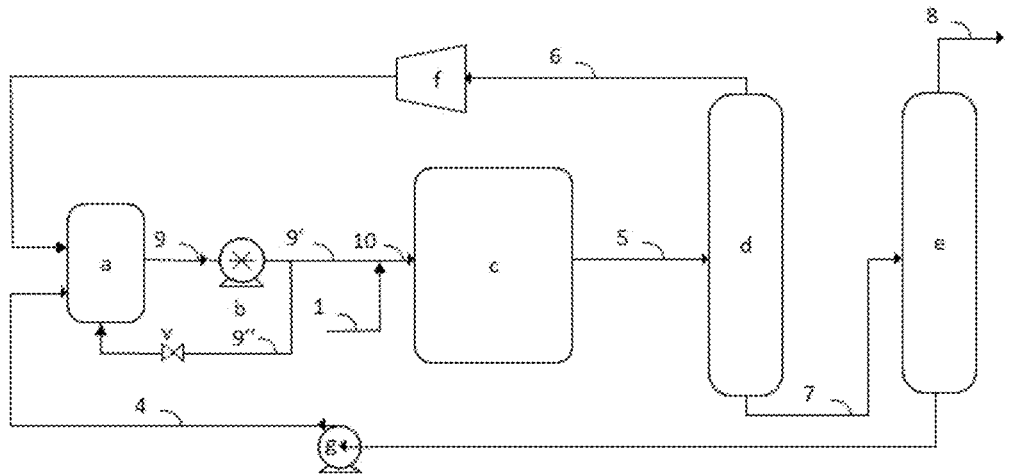
FIG. 5 is a diagram of an ethylene oligomerization installation according to a fourth variant of the invention.

FIG. 5 is a diagram of an installation implementing an ethylene oligomerization process according to a fourth variant of the invention: relative to the preceding variants, the solvent 4 is, here, placed in contact with recycled ethylene 6 in the gas/liquid mixture vessel a. The solvent 4 is fed into the gas/liquid mixture vessel a via the pump g, the delivery pressure of which is 28 bar absolute. The two-phase output 9 from the gas/liquid mixture vessel, at 28 bar absolute, is sent to the MPP pump b. A recirculation loop 9" at the outlet of the MPP pump b, piloted by a valve v, returns part of the stream exiting the MPP pump to the inlet of the gas/liquid mixture vessel a. This cycling from the outlet of the MPP pump to the inlet of the vessel a has two advantages. Firstly, it allows better control of the functioning of the pump by ensuring good control of the pump flow rate. Secondly, it generates a certain amount of turbulence in the gas/liquid mixture vessel, which has a tendency to homogenize the gas/liquid flow exiting the vessel a and to ensure good dispersion of the gas in the liquid in the vessel a: it avoids any phase segregation, and as such, in this vessel, there is organization of the phases in the form of bubbles dispersed in a liquid. The rest of the stream 9' exiting the MPP pump b is mixed with the stream 1 of fresh ethylene, and then sent in the form of stream 10 to the reactor c. This recirculation loop may advantageously apply in all the other variants of the invention.

This configuration corresponds to a case where the reactor is operated at a pressure intermediate between that of the first fractionating column d and the pressure at which the fresh ethylene 1 is available. The use of the multiphase pump b makes it possible to raise the recycled ethylene 6/recycled solvent 4 mixture to the pressure of the reactor c, which is below the pressure at which the fresh ethylene 1 is available. Said fresh ethylene may thus be introduced directly, i.e. without any compression means, under the control of an expansion valve for adjusting its pressure to that of the reactor c.

Figure 6:
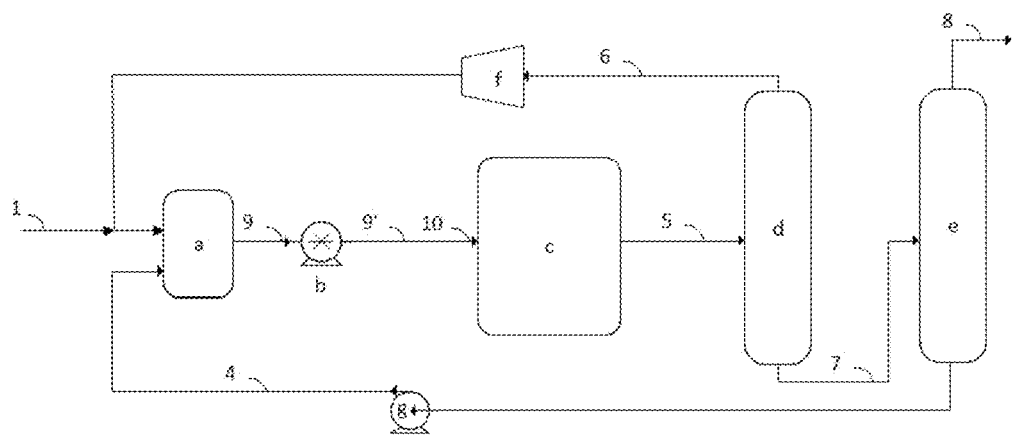
FIG. 6 is a diagram of an ethylene oligomerization installation according to a fifth variant of the invention.

FIG. 6 is a diagram of an installation implementing an ethylene oligomerization process according to a fifth variant of the invention: relative to the fourth variant of FIG. 5, there is no longer a recycling loop 9" from the outlet of the MPP pump b to the inlet of the vessel a, and all of the recycled ethylene stream 6 and of the fresh ethylene stream 1 which feeds the gas/liquid mixture vessel with gas, with the liquid solvent 4. Stream 9 exiting the vessel a feeds the MPP pump b, and all of stream 9' exiting the pump b constitutes stream 10 feeding the reactor c.

Figure 7:
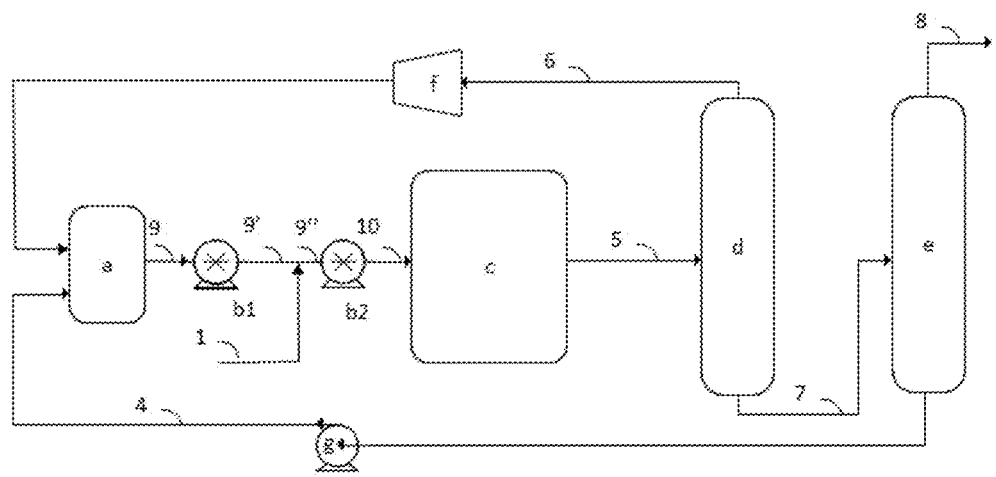
FIG. 7 is a diagram of an ethylene oligomerization installation according to a sixth variant of the invention.

FIG. 7 is a diagram of an installation implementing an ethylene oligomerization process according to a sixth variant of the invention: relative to the fifth variant of FIG. 6, this variant uses two MPP pumps b1 and b2. The recycled ethylene stream 6 feeds the vessel a with the solvent stream 4. Stream 9 exiting the vessel a feeds the first pump b1. Stream 9' exiting pump b1 is mixed with stream 1 of fresh ethylene into a stream 9" which feeds the second pump b2, of which the outlet stream 10 feeds the inlet of the reactor c.

This configuration corresponds to a case in which the pressure of the first column d is less than the pressure at which the fresh ethylene 1 is available, as in the case of FIG. 5, but in which the pressure of the reactor c is higher than that at which the fresh ethylene 1 is available. The difference from the configuration of FIG. 5 is that a second multiphase pump, b2, is used downstream of the mixture between the fresh ethylene 1 and the gas/liquid mixture obtained from the gas/liquid mixture vessel a is compressed to the pressure value of the fresh ethylene 1 by a first multiphase pump b1.

Figure 8:
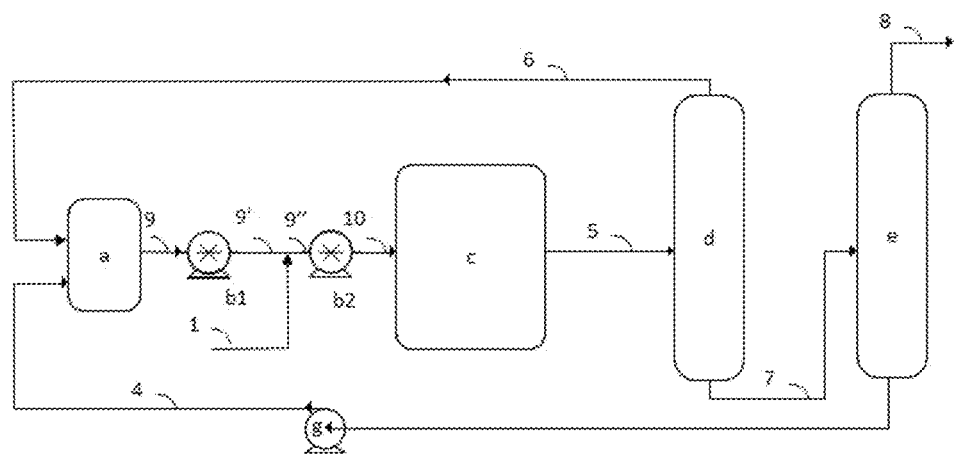
FIG. 8 is a diagram of an ethylene oligomerization installation according to a seventh variant of the invention.

FIG. 8 is a diagram of an installation implementing an ethylene oligomerization process according to a seventh variant of the invention: relative to the sixth variant of FIG. 7, the difference here is that the recycled ethylene stream 6 is not compressed before entering the gas/liquid mixture vessel a, there is no compressor f between the outlet of the column head fraction d and the inlet of the vessel a. By omitting the compressor in this manner is in fact possible in certain cases, notably when the reactor c operates at a lower pressure, the MPP pump b then being sufficient to give the desired pressure to the stream 10 entering the reactor c. This configuration thus corresponds to a case where all the compression of the recycled gas is performed by multiphase pumps: There is thus no longer a compressor.

EXAMPLES

Example 1 (Comparative)

This example implements the process as shown in FIG. 1. Besides the fact of using conventional technologies, pumps and compressors, the operating conditions (pressure, temperature and flow rate of reagents and of solvent) are identical to those adopted in the case of Example 2 below.

Example 2 (According to the Invention)

This example is in accordance with the first variant of the invention according to FIG. 2, with saturation with fresh ethylene of the recycled solvent compressed to 64 bar absolute.

The operating conditions at the inlet of the MPP pump b are collated in table 1 below.

| | Units | MPP inlet (first stage) |
|---|---|---|
| Phase | | Mixed |
| Total flow rate (liquid + gas) | $m^3/h$ | 150 |
| temperature | ° C. | 53.5 |
| pressure | bar absolute | 28 |
| Gas phase flow rate | $m^3/h$ | 86.3 |
| Liquid phase flow rate | $m^3/h$ | 63.7 |
| GVF | % | 58 |

The multiphase pump b was dimensioned based on the conditions shown in Table 1, with the results detailed in Table 2 below. To achieve the reactor pressure of 64 bar absolute, a pump b of the order of 330 kW and eight compression stages are chosen. Calculation of the GLR (gas-liquid ratio) is performed in the following manner:

$$GLR = Q_{vapour}(m^3/h) / Q_{liquid}(m^3/h)$$

| | | | | Etage | | | |
|---|---|---|---|---|---|---|---|
| unité | Débit total d'entrée $m^3/h$ | GLR à l'entrée de l'étage | GVF entrée % | Augmentation de pression homogéne bar | Augmentation de Température ° C. | Pression entrée Bar absolu | Pression sortie Bar absolu |
| 1 | 150 | 1.43 | 58.8 | 2.18 | 1.3 | 28.0 | 30.2 |
| 2 | 135 | 1.05 | 51.2 | 2.66 | 1.35 | 30.2 | 32.8 |
| 3 | 119 | 0.82 | 45.1 | 3.27 | 1.43 | 32.8 | 36.1 |
| 4 | 103 | 0.57 | 36.3 | 3.99 | 1.53 | 36.1 | 40.1 |
| 5 | 87 | 0.33 | 24.8 | 4.81 | 1.58 | 40.1 | 44.9 |
| 6 | 72 | 0.09 | 8.3 | 5.73 | 1.54 | 44.9 | 50.6 |
| 7 | 66 | 0 | 0 | 6.11 | 1.47 | 50.6 | 56.8 |
| 8 | 66 | 0 | 0 | 6.11 | 1.47 | 56.8 | 62.9 |

It is observed that the increase in pressure promotes the absorption of the gas in the liquid, which brings about a reduction of the gas flow rate in each stage. The total gas flow rate is reduced by 100%, which promotes the ethylene oligomerization reaction since, at the reactor inlet, all the ethylene has passed into the liquid phase: any piercing problem in the gaseous headspace of the reactor or any entrainment of ethylene bubbles in the recirculation loop with heat exchange around the reactor c is avoided.

Figure 9:
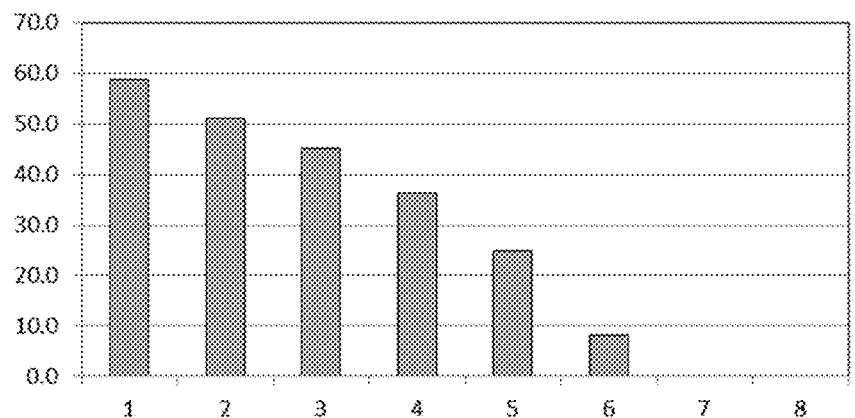
FIG. 9 is a graph representing the change in the gas volume fraction GVF at the inlet of each of the stages of the multiphase pump used in accordance with the invention according to FIG. 2.

The gas volume fraction varies from 58% at the inlet to 0% at the outlet of the sixth stage: FIG. 9 shows the change in GVF at the inlet of the stages mounted in series in the pump (the number 9 represents the outlet of the last stage).

The increase in liquid flow rate also promotes the pressure difference per stage: it is proportionately greater the lower the gas flow rate, i.e. the more the absorption of gas in the solvent increases.

Investment and energy consumption cost data were compared between Comparative Example 1 (FIG. 1) and Example 2 according to the invention (FIG. 2): a total reduction of the installation cost of 22% was observed for Example 2, relative to Comparative Example 1. This reduction is a consequence of a 33% reduction in the cost of the compressor f on account of the reduction of its operating flow rate. The 37% reduction in the cost of the solvent pump g should also be noted, on account of the reduction of its delivery pressure.

As regards the power consumption: a 40% reduction in consumption is observed for Example 2 relative to Example 1, mainly on account of the 57% reduction of the power of the compressor f.

Example 3 (According to the Invention)

This example is in accordance with the second variant of the invention according to FIG. 3, with saturation with fresh ethylene of the recycled solvent and compression of the recycled ethylene to 28 bar absolute. The operating conditions and volume flow rate at the inlet of the multiphase pump b are indicated in table 3 below:

|  | Units | MPP inlet (first stage) |
|---|---|---|
| Phase |  | Mixed |
| Total flow rate (liquid + gas) | m³/h | 353 |
| temperature | ° C. | 53.5 |
| pressure | bar absolute | 28 |
| Gas phase flow rate | m³/h | 287 |
| Liquid phase flow rate | m³/h | 65.5 |
| GVF | % | 81 |

The multiphase pump b was dimensioned based on the conditions given in Table 3, giving the results detailed in Table 4 below. To achieve the reactor pressure of 64 bar absolute, an MPP pump of the order of 730 kW and 16 compression stages were chosen. Pump 2 includes two series of stages, the first series including 10 compression stages, the second 6 stages.

| | | | Etage | | | |
|---|---|---|---|---|---|---|
| unité | Débit total d'entrée m³/h | GLR à l'entrée de l'étage | GVF entrée % | Augmentation de pression homogéne bar | Augmentation de Température ° C. | Pression entrée Bar absolu |
| 1 | 353 | 4.39 | 81.5 | 0.71 | 28.0 | 28.7 |
| 2 | 344 | 4.24 | 80.9 | 0.77 | 28.7 | 29.5 |
| 3 | 334 | 4.09 | 80.4 | 0.84 | 29.5 | 30.3 |
| 4 | 324 | 3.94 | 79.8 | 0.92 | 30.3 | 31.2 |
| 5 | 313 | 3.78 | 79.1 | 1 | 31.2 | 32.2 |
| 6 | 302 | 3.61 | 78.3 | 1.11 | 32.2 | 33.4 |
| 7 | 291 | 3.44 | 77.5 | 1.22 | 33.4 | 34.6 |
| 8 | 279 | 3.26 | 76.5 | 1.36 | 34.6 | 35.9 |
| 9 | 267 | 3.07 | 75.4 | 1.51 | 35.9 | 37.4 |
| 10 | 254 | 2.88 | 74.2 | 1.7 | 37.4 | 39.1 |
| 11 | 185 | 1.83 | 64.7 | 2.91 | 39.1 | 42.1 |
| 12 | 169 | 1.59 | 61.4 | 3.38 | 42.1 | 45.4 |
| 13 | 153 | 1.34 | 57.3 | 3.91 | 45.4 | 49.3 |
| 14 | 137 | 1.1 | 52.4 | 4.51 | 49.3 | 53.9 |
| 15 | 122 | 0.86 | 46.2 | 5.15 | 53.9 | 59.0 |
| 16 | 106 | 0.63 | 38.7 | 5.81 | 59.0 | 64.8 |

It is observed that the increase in pressure promotes the absorption of the gas in the liquid, which brings about a reduction of the gas flow rate in each stage, as shown in FIG. 6. The total gas flow rate is reduced by 86%, which promotes the ethylene oligomerization reaction: at the inlet of the reactor c, a large proportion of the solvent is saturated with ethylene, and thus any piercing problem in the gaseous headspace of the reactor or any entrainment of ethylene bubbles in the recirculation/cooling loop with heat exchange around the reactor is avoided.

Figure 10:
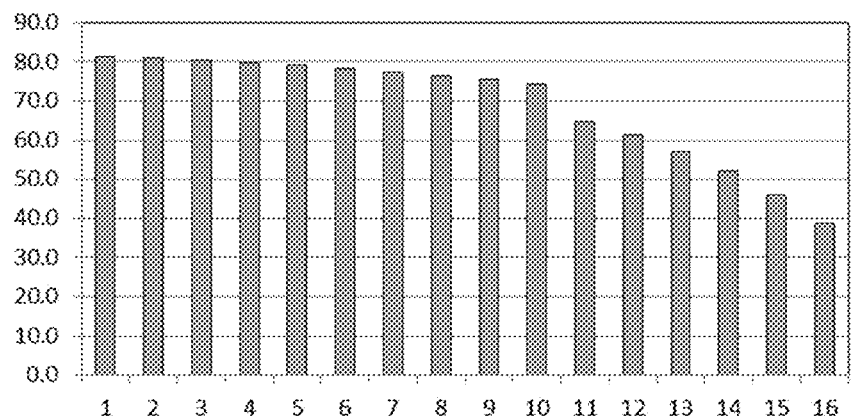
FIG. 10 is a graph representing the change in the gas volume fraction GVF at the inlet of each of the stages of the multiphase pump used in accordance with the invention according to FIG. 3.

The volume fraction varies from 81% at the inlet to 39% at the outlet of the sixteenth stage. FIG. 10 shows the change in GVF at the inlet of the stages mounted in series in the pump. The increase in liquid flow rate also promotes the pressure difference per stage. The compression difference per stage is proportionately greater the lower the gas flow rate, the more the gas is dissolved/absorbed in the solvent.

Investment and energy consumption cost data were compared between Comparative Example 1 (FIG. 1) and Example 3 according to the invention (FIG. 3): a total reduction of the installation cost of 30% is observed in the case of Example 3, relative to Example 1. This reduction is explained by a 48% reduction in the cost of the compressor f on account of the reduction of its operating flow rate and the delivery pressure. The 37% reduction in the cost of the solvent pump g should also be noted, on account of the reduction of its delivery pressure.

As regards the power consumption: the total reduction of Example 3 relative to Example 1 is 40%, mainly on account of the 79% reduction of the power of the compressor f.

It is thus observed that the invention is very efficient both in terms of installation investment and of running costs, while at the same time maintaining or increasing the production yield of the oligomerization products. The gain is spectacular: it was unexpected that adding an MPP pump in this way would allow these results.

From the set of variants illustrated in FIGS. 1 to 8, it is seen that the invention allows numerous configurations and that it is thus very flexible in its implementation. It can thus be adapted to varied dimensionings of reactors and to reactor operating pressures within a wide range of values.

It is pointed out that combining two or more of these variants remains within the context of the invention, when they are technically compatible. Thus, the recirculation loop at the pump outlet according to FIG. 5 may be applied to the other installation configurations of the other figures, and to the process of the invention as generally defined.

The invention claimed is:

1. A process for the oligomerization of C2 to C4 olefin(s) in a gas/liquid or all-liquid oligomerization reactor (c) using a solvent, an oligomerization catalyst and olefin(s), comprising performing compression and premixing between a liquid phase comprising the solvent and a gaseous phase comprising the gaseous olefin(s) by a multiphase pump (b), with partial or total dissolution of the olefin(s) of the gaseous phase in the liquid phase and/or premixing between the two phases, before introduction of the premix obtained into said reactor.

2. The process according to claim 1, wherein the multiphase pump (b) ensures total dissolution of the gaseous olefin(s) in the liquid phase, until an entirely liquid phase is obtained at the pump outlet.

3. The process according to claim 1, wherein the multiphase pump (b) is fed with the liquid phase and the gaseous phase in relative proportions corresponding to a gas volume fraction GVF of at least 5%.

4. The process according to claim 1, wherein the multiphase pump (b) ensures a pressure rise of the mixture of the liquid phase and of the gaseous phase up to the pressure in the oligomerization reactor.

5. The process according to claim 1, wherein the liquid phase and the gaseous phase which are compressed and premixed by the multiphase pump (b) before introduction into the reactor (c) comprise at least partly, respectively, recycled solvent and/or recycled olefin(s), which is/are recycled by separation downstream of the reactor (c).

6. The process according to claim 1, wherein a first separation is performed of the reaction mixture obtained from the oligomerization performed in the reactor (c), said mixture comprising the olefin(s) introduced, the α-olefin(s) produced, solvent, an oligomerization catalyst, and oligomerization products, so as to obtain a head fraction containing olefin(s) and at least one tail fraction.

7. The process according to claim 6, wherein at least part of the head fraction containing olefin(s), referred to as the recycled olefin(s), obtained from the first separation, is recycled, and in that this or these recycled olefin(s) form(s) part of the gaseous phase on which the compression and premixing by the multiphase pump are performed.

8. The process according to claim 1, wherein a second separation of at least a portion of the tail fraction obtained from the separation of the mixture is performed into at least a head fraction enriched in oligomerization products and a tail fraction enriched in solvent, or into at least one head fraction enriched in solvent and a tail fraction enriched in oligomerization products.

9. The process according to claim 8, wherein at least a portion of the fraction enriched in solvent, known as recycled solvent, obtained from the second separation, is recycled, and this recycled solvent forms part of the liquid phase on which the compression and premixing by the multiphase pump are performed.

10. The process according to claim 1, wherein the gaseous phase containing the gaseous olefin(s) which is compressed and premixed by the multiphase pump comprises fresh olefin(s) and/or the recycled olefin(s) at the outlet of the reactor (c).

11. The process according to claim 10, wherein part of the gaseous olefin(s) feeding the oligomerization reactor, which comprises all or part of the recycled olefin(s) and/or all or part of the fresh olefin(s), is (are) introduced into the outlet of the multiphase pump or into the inlet of the oligomerization reactor.

12. The process according to claim 10, wherein part of the gaseous olefin(s) feeding the oligomerization reactor is (are) introduced into the outlet of the multiphase pump or into the inlet of the oligomerization reactor.

13. The process according to claim 1, wherein the multiphase pump (b) is fed with gaseous phase and with liquid phase via a device for regulating the flow rate, or a device for regulating the level, which is positioned upstream of said multiphase pump and is itself fed, on the one hand, with fresh or recycled olefin(s) or with a mixture of fresh and recycled olefin(s), and, on the other hand, with solvent.

14. The process according to claim 1, wherein the multiphase pump (b) ensures a pressure rise of the mixture of the liquid phase and of the gaseous phase up to a pressure of at least 20 bar absolute.

15. The process according to claim 1, wherein a first separation is performed by one or more first fractionation columns downstream of the reactor (c), of the reaction mixture obtained from the oligomerization performed in the reactor (c), said mixture comprising the olefin(s) introduced, the α-olefin(s) produced, solvent, an oligomerization catalyst, and oligomerization products, so as to obtain a head fraction containing olefin(s) and at least one tail fraction.

16. The process according to claim 1, wherein a second separation of at least a portion of the tail fraction obtained from the separation of the mixture is performed with one or more second fractionating column(s) downstream of the first column(s), into at least a head fraction enriched in oligomerization products and a tail fraction enriched in solvent, or into at least one head fraction enriched in solvent and a tail fraction enriched in oligomerization products.

17. The process according to claim 1, wherein the multiphase pump (b) is fed with gaseous phase and with liquid phase via a device for regulating the flow rate, or a device for regulating the level, which is a gas/liquid mixture vessel (a), which is positioned upstream of said multiphase pump and is itself fed, on the one hand, with fresh or recycled olefin(s) or with a mixture of fresh and recycled olefin(s), and, on the other hand, with solvent, which is recycled solvent.

18. The process according to claim 1, wherein the olefin(s) which are recycled by separation at the reactor (c) outlet is (are) compressed before introduction into the reactor (c) by a plurality of n compressors (f1, f2, fn) in series, in that the multiphase pump (b) comprises a plurality of m successive stages (b1, b2, bm), and in that, at the outlet of each of the n−1 compressors, a first stream feeds the next compressor and a second stream feeds the inlet of a stage of the multiphase pump.

19. An installation for the oligomerization of C2-C4 olefins, comprising a gas/liquid or all-liquid oligomerization reactor (c) using a solvent, an oligomerization catalyst and said olefins, wherein said installation comprises a multiphase pump (b) which ensures the compression and premixing between a liquid phase comprising the solvent and a gaseous phase comprising the gaseous olefin(s), with partial or total dissolution of the olefin(s) of the gaseous phase in the liquid phase and/or premixing between the two phases, with introduction of the premix obtained into said reactor (c).

20. An installation for performing the process according to claim 1, which comprises: —at least one oligomerization reactor (c) using C2-C4 olefin(s), solvent and oligomerization catalyst, —at least two successive separation columns (d, e) in series downstream of the oligomerization reactor (c), —at least one gas/liquid mixture vessel (a) fed with recycled solvent obtained from the second separation column (e) and with fresh olefin(s) and/or recycled olefin(s) obtained from the first separation column, said vessel feeding a multiphase pump (b), —said multiphase pump (b) fed with fresh and/or recycled olefin(s) and with fresh and/or recycled solvent at least partly via the gas/liquid mixture vessel and feeding the reactor (c).

* * * * *